United States Patent
Bouvenot et al.

(10) Patent No.: US 8,461,359 B2
(45) Date of Patent: Jun. 11, 2013

(54) SHORT SYNTHETIC PATHWAY FOR 1,6:2,3-DIANHYDRO-β-D-MANNOPYRANOSE

(75) Inventors: Laurent Bouvenot, Paris (FR); Paul Cruciani, Paris (FR); Denis Largeau, Paris (FR); Jean-Claude Rovera, Paris (FR)

(73) Assignee: Sanofi, Paris (FR)

( * ) Notice: Subject to any disclaimer, the term of this patent is extended or adjusted under 35 U.S.C. 154(b) by 202 days.

(21) Appl. No.: 13/119,332

(22) PCT Filed: Sep. 15, 2009

(86) PCT No.: PCT/FR2009/051730
§ 371 (c)(1),
(2), (4) Date: May 9, 2011

(87) PCT Pub. No.: WO2010/031954
PCT Pub. Date: Mar. 25, 2010

(65) Prior Publication Data
US 2011/0224446 A1    Sep. 15, 2011

(30) Foreign Application Priority Data

Sep. 16, 2008   (FR) ..................... 08 05063

(51) Int. Cl.
    *C07D 493/18*    (2006.01)
(52) U.S. Cl.
    USPC ........................................ 549/386

(58) Field of Classification Search
    USPC ........................................... 549/386
    See application file for complete search history.

(56) References Cited

PUBLICATIONS

Bailliez, V. et al., "A Practical Large-Scale Access to 1,6-Anhydro-β-$_D$-hexopyranoses by a Solid-Supported Solvent-Free Microwave-Assisted Procedure," Synthesis (2003), vol. 7, pp. 1015-1017.
Miljkovic, Dusan et al., "A convenient route to 6-functionalized derivatives of $_D$-glucal," Carbohydrate Research (1989), vol. 193, pp. 275-278.
International Search Report dated Feb. 2, 2010.

*Primary Examiner* — Bernard Dentz
(74) *Attorney, Agent, or Firm* — Scully, Scott, Murphy & Presser, P.C.

(57) ABSTRACT

The invention relates to a method for preparing 1,6:2,3-dianhydro-β-D-mannopyranose and is characterized in that it includes a step of cyclizing the compound B, where R is an activating agent, in the presence of a base selected from among ammonium hydroxides and mineral bases.

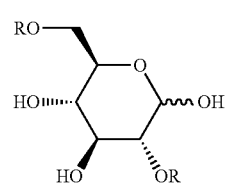

12 Claims, No Drawings

SHORT SYNTHETIC PATHWAY FOR 1,6:2,3-DIANHYDRO-β-D-MANNOPYRANOSE

The present invention relates to a novel process for the preparation of 1,6:2,3-dianhydro-β-D-mannopyranose, denoted hereinafter as "Cerny epoxide" or "compound (I)", corresponding to the following formula, in which the bold lines represent bonds situated above the pyranose ring:

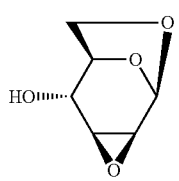
(I)

or, according to another representation:

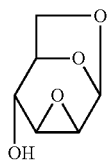
(I)

Compound (I) and more generally the compounds of the family of the 1,6:(2,3 and 3,4)-dianhydro-β-D-hexopyranoses have essentially been described a Czech chemist, Miloslav Cerny. Three access routes to the Cerny epoxide (I) from compound 1 (1,6:3,4-dianhydro-2-O-tosyl-β-D-galactopyranose) are found in the literature:

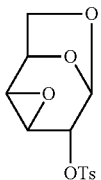
1

The compound 1 is obtained from levoglucosan 2 (or 1,6-anhydro-β-D-glucopyranose), as represented below (M. Cerny et al., Collect. Czech. Chem. Commun., 1961, vol. 26, pp. 2542-2550):

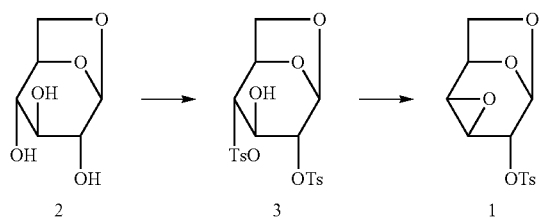 [SMILES: OC1C2COC(O2)C(O)C1O ; Cc1ccc(S(=O)(=O)OC2C3COC(O3)C(OS(=O)(=O)c3ccc(C)cc3)C2O)cc1 ; Cc1ccc(S(=O)(=O)OC2C3OCC(O3)C3OC32)cc1]

The ditosylated derivative 3 (1,6-anhydro-2,4-di-O-tosyl-β-D-glucopyranose) is selectively obtained (80%). The remaining 20% are essentially composed of the tritosylated derivative. The overall yield for the conversion of compound 2 to compound 1 is 55%.

There are many access routes to levoglucosan 2; those most used industrially are, in addition to the pyrolysis of starch and cellulose described since the 1960s, the cyclisations in a basic or acidic medium of D-glucose represented below:

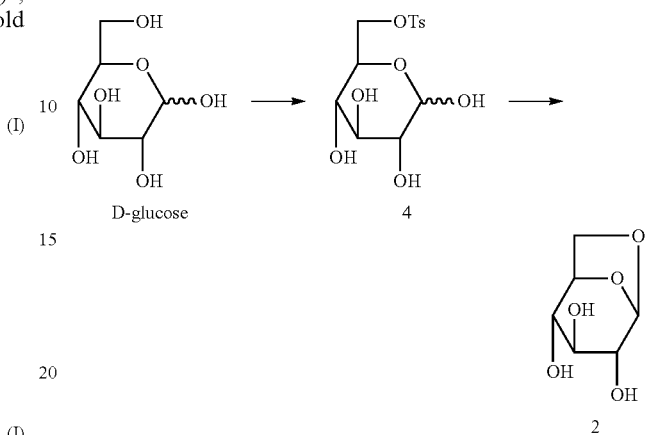

Cyclisation in a Basic Medium

4: 6-O-tosyl-D-glucopyranose

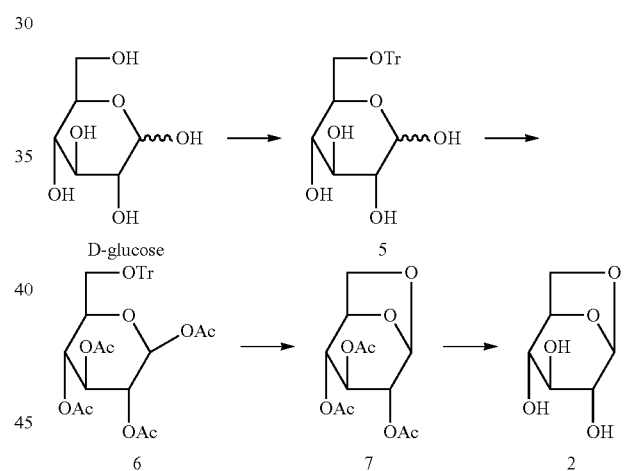

Cyclisation in an Acidic Medium

5: 6-O-trityl-D-glucopyranose

6: 1,2,3,4-tetra-O-acetyl-6-O-trityl-β-D-glucopyranose

7: 1,6-anhydro-2,3,4-tri-O-acetyl-β-D-glucopyranose

The cyclisation in a basic medium (M. A. Zottola et al., J. Org. Chem., 1989, vol. 54, pp. 6123-6125; M. Akagi et al., Chem. Pharm. Bull., 1962, vol. 10, pp. 905-909) is reflected by a low yield (15%). Furthermore, it is necessary to acetylate the crude levoglucosan 2 in order to allow it to be isolated. With regard to the route of cyclisation in an acidic medium (M. V. Rao et al., Carbohydrate Research, 1987, vol. 162, 141-144; R. L. Wistler et al., Methods Carbohydr. Chem., 1972, vol. 6, pp. 411-412; E. Zara-Kaczian et al., 1982, vol.

111, No. 3, pp. 271-283; E. Zara-Kaczian et al., Acta Chemica Acad. Scient. Hung., 1978, vol. 96, No. 3, pp. 311-313), it is described with a better yield (70%) but it comprises a further two stages.

The three access routes to the Cerny epoxide (I) from compound 1 are as follows.

Route 1:

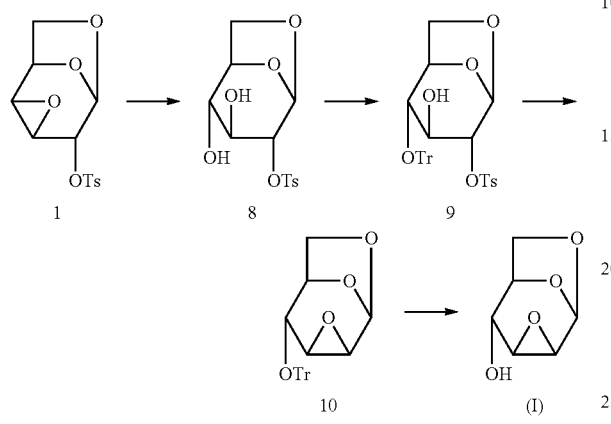

8: 1,6-anhydro-2-O-tosyl-β-D-glucopyranose

9: 1,6-anhydro-2-O-tosyl-4-O-trityl-β-D-glucopyranose

10: 1,6:2,3-dianhydro-4-O-trityl-β-D-glucopyranose

In addition to the number of stages necessary to arrive at the Cerny epoxide (I), this sequence comprises, inter alia, the difficulty of selectively hydrolysing the 3,4-anhydro functional group during the first stage. The hydroxyl in the 4 position of the monotosylated derivative 8 is subsequently protected by a trityl group (Tr) in order to prevent the epoxide from migrating during the cyclisation in the presence of sodium ethoxide (EtONa).

Route 2:

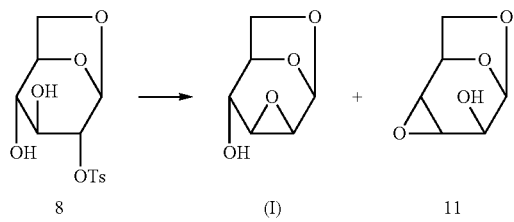 [SMILES: Cc1ccc(S(=O)(=O)OC2C3OCC(O3)C(O)C2O)cc1 ; OC1C2COC(O2)C2OC12 ; OC1C2OCC(O2)C2OC12 ; "(I)"]

According to M. Cerny et al. (Synthesis, 1972, 698-699), the Cerny epoxide (I) can be obtained from the derivative 8 in the presence of Amberlite IRA 400/OH⁻ resin. However, prolonged contact with the resin results in the migration of the epoxide into the 3,4 position and the formation of the derivative 11 (1,6:3,4-dianhydro-β-D-altropyranose). The difficulty in selectively obtaining the compound (I) thus remains. The starting compound 8 is itself also difficult to selectively obtain, as mentioned above.

Route 3:

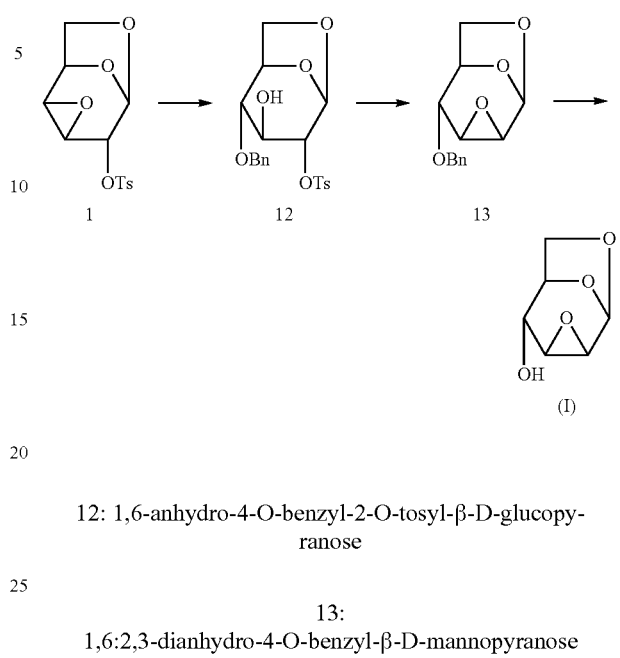

12: 1,6-anhydro-4-O-benzyl-2-O-tosyl-β-D-glucopyranose

13: 1,6:2,3-dianhydro-4-O-benzyl-β-D-mannopyranose

This variant makes it possible to cyclise to give the dianhydro derivative 13 without migration of epoxide (T. Trnka et al., Collect. Czech. Chem. Commun., 1971, vol. 36, pp. 2216-2225; M. Cerny et al., Collect. Czech. Chem. Commun., 1968, vol. 33, pp. 1143-1156). Nevertheless, it comprises a large number of stages to provide the Cerny epoxide (I) from D-glucose.

In conclusion, the three access routes described above for the preparation of the Cerny epoxide (I) have respectively 10, 8 and 9 stages starting from D-glucose (using, in order to obtain levoglucosan 2, the cyclisation in an acidic medium, which is the route described with the better yield) and have, for overall yield, 0.5%, 10% and 13% respectively for routes 1, 2 and 3.

Furthermore, V. Bailliez et al. have described, in Synthesis, 2003, No. 7, 1015-1017, an access route to 1,6:3,4-dianhydro-β-D-altropyranose which is accompanied by formation of a minor amount of 1,6:2,3-dianhydro-β-D-mannopyranose as byproduct. According to these authors, the Cerny epoxide can be formed from a precursor cyclised beforehand between the 1 and 6 positions or else an N-1 precursor of Cerny epoxide acetylated in the 4 position can be obtained, at a level of 5%, in several stages from 1,3,4-tri-O-acetyl-2,6-di-O-tosyl-glucose subjected to alumina, irradiation under microwaves and per-O-acetylation.

In view of the costs of labour and starting materials, and in order to obtain the compound (I) on the industrial scale, it is necessary to envisage a shorter and thus more profitable synthesis. The inventors have now found an access route to the compound (I) in two stages starting from D-glucose which meets the abovementioned requirements.

The process according to the invention comprises the stages represented below in Scheme 1.

Scheme 1:

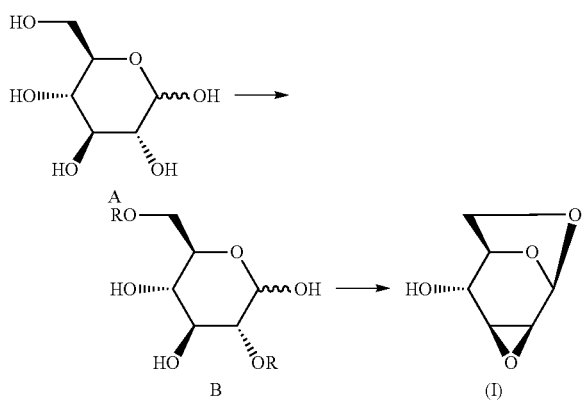

A subject-matter of the invention is thus a process for the preparation of compound (I), characterized in that it comprises a stage of cyclisation of compound B, in which R represents an activating group, in the presence of a base.

"Activating agent" is understood to mean an agent which makes possible the departure of the leaving group —OR and which promotes the cyclisation reaction between the 1 and 6 positions of compound B, for example a tosyl, mesyl, benzenesulphonyl or benzenesulphonyl derivative halide, such as a p-halobenzenesulphonyl halide. The compound B is thus such that R represents a tosyl, mesyl, benzenesulphonyl or p-halobenzenesulphonyl group.

In the case of tosyl chloride (TsCl), the -OTs group is an excellent leaving group. Use is thus advantageously made of tosyl chloride as activating agent, in a solvent, such as pyridine.

The base used during the cyclisation stage defined above is chosen from ammonium hydroxides and inorganic bases. The inorganic bases which can be used can be strong inorganic bases (for example, sodium hydroxide or potassium hydroxide) or weak inorganic bases, in particular of solid type (for example, potassium carbonate, sodium carbonate or caesium carbonate).

"Ammonium hydroxide" is understood to mean a compound of formula $N^+(R_1)(R_2)(R_3)(R_4)\,OH^-$, in which $R_1$, $R_2$, $R_3$ and $R_4$, which are identical or different, represent alkyl groups, the said alkyl groups being saturated and linear or branched aliphatic groups comprising from 1 to 4 carbon atoms. An ammonium hydroxide used during the reaction for cyclisation of compound B can, for example, consist of tetrabutylammonium hydroxide.

The stage of cyclisation of compound B is carried out in an appropriate solvent chosen, according to the nature of the base used, according to the knowledge of a person skilled in the art in this field. The reaction can, for example, be carried out in isopropanol, dichloromethane or acetonitrile, or else in a binary mixture of these solvents.

Use is made, for example, as solvent, of an isopropanol/dichloromethane mixture comprising, for example, approximately 5% by volume of dichloromethane, when the base used is tetrabutylammonium hydroxide. In this case, the cyclisation reaction is advantageously carried out at low temperature, in particular at a temperature of less than or equal to 0° C., the presence of dichloromethane making it possible to dissolve compound B at low temperature. It is possible, for example, to carry out the cyclisation reaction at a temperature of between −10° C. and 0° C., for example at approximately −5° C.

When the base used during the cyclisation reaction is caesium carbonate, use is advantageously made of acetonitrile as solvent, at a temperature of approximately 40° C.

As known to a person skilled in the art, the temperature of the reaction medium during the cyclisation stage is adjusted according to the solvent/base pair used, so as to optimize the reaction kinetics.

Compound (I) is obtained, according to the process of the invention, with a selectivity of 65 to 85% from intermediate B. The chemical yield of this stage, calculated with regard to the isolated product, is at least 60%.

Another subject-matter of the invention is a process for the preparation of compound (I), characterized in that it comprises a stage of activation of compound A (D-glucose), which makes it possible to obtain compound B, and then a stage of cyclisation of compound B in the presence of a base, as defined above.

The stage of activation of compound A can be carried out using an activating agent as defined above. This stage is advantageously carried out using a tosyl, mesyl, benzenesulphonyl or benzenesulphonyl derivative halide, such as a p-halobenzenesulphonyl halide, in a solvent, such as pyridine.

The invention is illustrated using the following examples, which describe in detail a process for the preparation of compound (I) in accordance with the invention, according to the following Scheme 2.

Scheme 2:

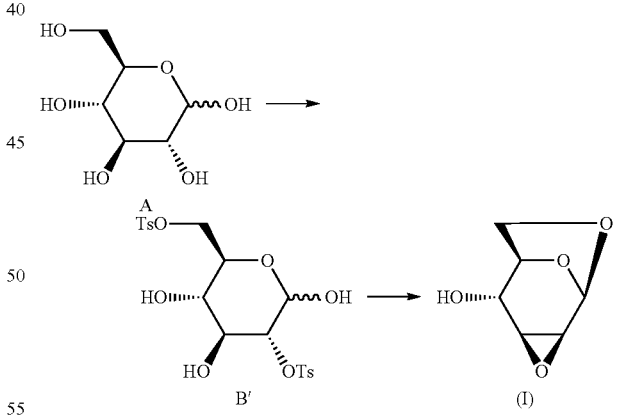

1) Preparation of Compound B' (2,6-Di-O-Tosyl-Glucopyranose)

100 g (0.55 mol) of D-glucose and 500 g of pyridine are charged to a 2 liter reactor equipped with a stirring system. The reaction medium is cooled to −10° C. The tosyl chloride solution is prepared in another 1 liter reactor: 212 g (1.12 mol) of tosyl chloride and 667 g of pyridine are introduced and stirring is carried out at 20° C. until complete dissolution is achieved. The contents of the 1 liter reactor are gradually transferred (in 4 to 5 h) into the 2 liter reactor while maintaining the temperature at −10° C. Rinsing is carried out with 39 g of pyridine and the reaction medium is kept stirred at −11° C. for 17 h.

An exchange of solvent is carried out by distillation, using demineralized water. The pyridine in the reaction medium has to be 5.20%; if this is not the case, a distillation is again carried out with 400 ml of water.

The reaction medium is cooled to 20° C. and 400 ml of demineralized water are introduced. In order to remove the monotosylated compound, 400 ml of dichloromethane, 48 g of hydrochloric acid and 33 ml of water are introduced. The mixture is left standing for 30 min and the pH, which has to be less than or equal to 1, is measured; if such is not the case, further hydrochloric acid is added dropwise until a pH ≦1 is obtained. Washing operations are then carried out with a sodium chloride solution (400 ml of water+40 g of sodium chloride) until a pH of approximately 5 to 5.5 is obtained.

Finally, the dichloromethane phase is concentrated on a rotary evaporator. The concentrate is taken up in 150 ml of dichloromethane and again concentrated. After having carried out this operation three times, compound B' is obtained in the form of a beige (cream) foam.

Weight of product expected=271 g.
Weight of product obtained=184 g.
Organic purity=81.6%, measured by HPLC (High Performance Liquid Chromatography).
Chemical yield=55%.

2) Preparation of Compound (I)

2.1: Cyclisation Carried Out Using Tetrabutylammonium Hydroxide 10 g of compound B' as obtained on conclusion of the preceding stage, 100 ml of isopropanol and 5 ml of dichloromethane are charged to a 1 liter reactor. The reaction medium is cooled to a temperature of −5° C. with stirring at 400 rev/min. 26.6 g of 40% tetrabutylammonium hydroxide in water are slowly run in (over approximately 30 min). The mixture is left stirring for 30 minutes and the reaction is halted by neutralizing the reaction medium with 12% hydrochloric acid until a pH of approximately 6 to 7 is obtained. The solvent is changed (replacing isopropanol with ethyl acetate) on a rotary evaporator with 6 ml of ethyl acetate. The estimated chemical yield at this stage is approximately 60%, the organic purity of compound (I) being 68%, measured according to the area of the peaks in gas chromatography.

The proton and carbon-13 NMR spectra of compound (I) are recorded on a Bruker 300 MHz device. The chemical shifts are expressed with respect to tetramethylsilane, to within 0.01 ppm for the proton spectrum and 0.1 ppm for the carbon-13 spectrum. The coupling constants are given as absolute value in Hz to within 0.5 Hz.

$^1$H NMR (CDCl$_3$): 2.67 (d, 1H, OH, J$_{4,OH}$ 5.5 Hz), 3.12 (d, 1H, H$_3$, J$_{2,3}$ 3.4 Hz), 3.42 (dd, 1H, H$_2$, J$_{2,3}$=J$_{2,1}$=3.0 Hz), 3.69 to 3.77 (m, 2H, H$_6$, H$_{6'}$), 3.89 (d, 1H, H$_4$, J$_{4,OH}$ 5.5 Hz), 4.40 (dm, 1H, H$_1$, J$_{1,2}$ 3.0 Hz).

$^{13}$C NMR: 49.3: C$_3$; 54.3: C$_2$; 65.6: C$_{6,6'}$; 67.1: C$_4$; 97.7: C$_1$; 74.2: C$_5$.

2.2: Cyclisation Carried Out Using Caesium Carbonate

In an alternative form, the procedure as indicated in Example 2.1 is carried out, but using caesium carbonate as base for the reaction for the cyclisation of compound B'. Use is made of 2 equivalents of caesium carbonate, with respect to the amount of compound B', namely 1.133 g of caesium carbonate per 1 g of compound B', in 10.5 ml of acetonitrile and at a temperature of approximately 40° C. The estimated chemical yield at this stage is approximately 80%, the organic purity of compound (I) thus obtained being 87%, measured according to the area of the peaks in gas chromatography.

The invention claimed is:

1. A process for the preparation of compound (I):

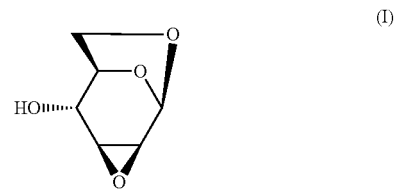

characterized in that it comprises a stage of cyclisation of compound B:

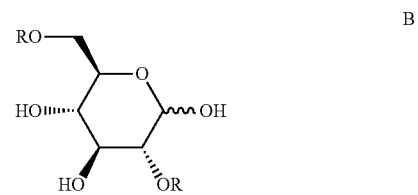

in which R represents an activating group, in the presence of a base chosen from ammonium hydroxides and inorganic bases.

2. The process according to claim 1, wherein said base is chosen from an ammonium hydroxide, sodium hydroxide, potassium hydroxide, potassium carbonate, sodium carbonate or caesium carbonate.

3. The process according to claim 1, wherein said base is tetrabutylammonium hydroxide.

4. The process according to claim 1, wherein said base is caesium carbonate.

5. The process according to claim 1, wherein the cyclisation stage is carried out in isopropanol, dichloromethane or acetonitrile, or in a binary mixture thereof.

6. The process according to claim 3, wherein the cyclisation stage is carried out in an isopropanol/dichloromethane mixture.

7. The process according to claim 6, wherein the cyclisation stage is carried out at a temperature of between −10° C. and 0° C.

8. The process according to claim 4, wherein the cyclisation stage is carried out in acetonitrile.

9. The process according to claim 8, wherein the cyclisation stage is carried out at a temperature of approximately 40° C.

10. The process according to claim 1, wherein compound B is such that R represents a tosyl, mesyl, benzenesulphonyl or p-halobenzenesulphonyl group.

11. The process according to claim 1, comprising:
a stage of activation of compound A:
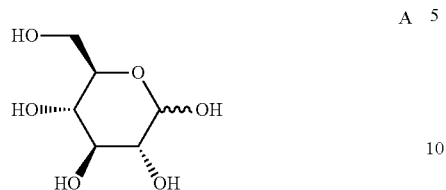
to obtain compound B,
followed by the stage of cyclisation of compound B.
12. The process according to claim 11, wherein the stage of activation of compound A is carried out using a tosyl, mesyl, benzenesulphonyl or p-halobenzenesulphonyl halide.
\* \* \* \* \*

UNITED STATES PATENT AND TRADEMARK OFFICE
CERTIFICATE OF CORRECTION

PATENT NO. : 8,461,359 B2  Page 1 of 1
APPLICATION NO. : 13/119332
DATED : June 11, 2013
INVENTOR(S) : Bouvenot et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 256 days.

Signed and Sealed this

Eighth Day of September, 2015

Michelle K. Lee
*Director of the United States Patent and Trademark Office*